United States Patent
Siess et al.

(10) Patent No.: US 9,533,084 B2
(45) Date of Patent: Jan. 3, 2017

(54) INTRAVASCULAR BLOOD PUMP

(71) Applicant: ABIOMED EUROPE GMBH, Aachen (DE)

(72) Inventors: Thorsten Siess, Wurselen (DE); Walid Aboulhosn, Betekhnay (LB)

(73) Assignee: ABIOMED EUROPE GMBH, Aachen (DE)

(*) Notice: Subject to any disclaimer, the term of this patent is extended or adjusted under 35 U.S.C. 154(b) by 0 days.

(21) Appl. No.: 14/371,154

(22) PCT Filed: Apr. 30, 2013

(86) PCT No.: PCT/EP2013/059055
§ 371 (c)(1),
(2) Date: Jul. 8, 2014

(87) PCT Pub. No.: WO2013/167432
PCT Pub. Date: Nov. 14, 2013

(65) Prior Publication Data
US 2015/0051435 A1      Feb. 19, 2015

(30) Foreign Application Priority Data

May 9, 2012 (EP) .................................... 12167341

(51) Int. Cl.
| A61N 1/362 | (2006.01) |
| A61M 1/10 | (2006.01) |
| A61M 1/12 | (2006.01) |

(52) U.S. Cl.
CPC .......... *A61M 1/1024* (2014.02); *A61M 1/101* (2013.01); *A61M 1/125* (2014.02)

(58) Field of Classification Search
CPC .. A61M 1/1024; A61M 1/125; A61M 1/1012; A61M 1/122
See application file for complete search history.

(56) References Cited

U.S. PATENT DOCUMENTS

| 4,753,221 A | 6/1988 | Kensey et al. |
| 4,919,647 A | 4/1990 | Nash |
| 5,749,855 A | 5/1998 | Reitan |

(Continued)

FOREIGN PATENT DOCUMENTS

| WO | WO-00/44417 | 8/2000 |
| WO | WO-03103745 A2 | 12/2003 |

(Continued)

OTHER PUBLICATIONS

Extended European Search Report for EP Appl. Ser. No. 12167341.2 dated Oct. 2, 2012.

(Continued)

*Primary Examiner* — Robert N Wieland
(74) *Attorney, Agent, or Firm* — Ropes & Gray LLP (57) ABSTRACT

A foldable, intravascularly insertable blood pump (10) comprises a foldable, radially delivering impeller (20) accommodated in a foldable housing or envelope (24). Axially before and behind the impeller a clearance (60) is provided between the impeller (20) and the front and back walls (32, 62) of the housing (24), the clearance being at least 0.2 mm. Preferably, the space defined between adjacent blades (54) of the impeller (20) is open towards the front wall (32) of the housing (24).

15 Claims, 8 Drawing Sheets

(56) References Cited

U.S. PATENT DOCUMENTS

| | | | |
|---|---|---|---|
| 5,827,171 A | 10/1998 | Dobak, III et al. | |
| 6,533,716 B1 | 3/2003 | Schmitz-Rode et al. | |
| 7,841,976 B2 | 11/2010 | McBride et al. | |
| 8,449,443 B2 * | 5/2013 | Rodefeld et al. | 600/16 |
| 2008/0103591 A1 | 5/2008 | Siess | |

FOREIGN PATENT DOCUMENTS

| | | |
|---|---|---|
| WO | WO-2006/051023 | 5/2006 |
| WO | WO-2010/119267 | 10/2010 |

OTHER PUBLICATIONS

International Search Report for PCT Appl. Ser. No. PCT/EP2013/059055 dated Aug. 27, 2013.
Office Action for EP Appl. Ser. No. 12167341.2 dated May 29, 2013.

\* cited by examiner

INTRAVASCULAR BLOOD PUMP

RELATED APPLICATIONS

This application is the U.S. National Stage of International Application Number PCT/EP2013/059055, filed Apr. 30, 2013, which claims priority to European Patent Application No. 12167341.2, filed May 9, 2012. The entire contents of the foregoing applications are hereby incorporated herein by reference.

FIELD OF THE INVENTION

The present invention relates to an intravascularly insertable blood pump comprising a housing in which a radially delivering impeller is arranged for rotation and further comprising a catheter accommodating a flexible shaft connected to an external motor for driving the impeller. More particularly, the present invention relates to an expandable intravascular blood pump.

BACKGROUND OF THE INVENTION

Rotary blood pumps are known which are inserted into the heart for supporting the pumping capacity of the natural heart. Insertion is performed intravascularly, namely through the blood vessel system of the patient. It is thus important that, upon insertion, the maximum diameter of the blood pump is small, preferably not exceeding 4 mm (12 French). Further, the blood pump should be flexible for the purpose of conforming to the bends of the vessel course.

The aforementioned rotary blood pumps that are currently in use are axially delivering blood pumps, i.e. they have an axial inlet and an axial outlet spaced therefrom, with an axially delivering impeller in between. The maximum pumped blood flow rate is thus limited by two factors, the cross sectional diameter through which the impeller delivers flow and the rotational speed at which the impeller is driven. Further increase of the diameter is limited by the blood vessel dimensions. Further increase of the rotational speed is difficult because of blood damage.

Therefore, foldable intravascular blood pumps have been proposed in which the impeller itself and the housing in which the impeller rotates can be deployed from a folded configuration into an unfolded, operational configuration (U.S. Pat. No. 4,753,221; U.S. Pat. No. 4,919,647; U.S. Pat. No. 5,749,855; U.S. Pat. No. 6,533,716; U.S. Pat. No. 7,841,976). If the insertion of foldable intravascular blood pumps is to be carried out through a catheter, the maximum diameter of the expandable blood pump should not exceed 4 mm (12 French), whereas, when deployed, the cross sectional diameter may be 9 mm (27 French).

A severe problem with foldable axial blood pumps is the required dimensional accuracy. The rotor must conform, within very close tolerances, to the inner shape of the housing for the purpose of attaining a flow rate of at least 2 l/min (liter per minute) at physiological pressure conditions and without excessively destroying blood. These requirements are difficult to fulfil with foldable blood pumps because of the flexibility of the foldable housing. More specifically, during use and in particular due to the bends in the vessel course, there is always the danger that the housing does not perfectly assume the predefined shape. Instead, unexpected forces acting locally on the flexible housing may cause the impeller to contact the inner wall of the housing and this may quickly lead to the destruction of the entire device or to unacceptable levels of blood damage and loss of parts in the patient's body.

There have also been other proposals for foldable blood pumps, such as in U.S. Pat. No. 5,827,171, which, instead of an impeller, employs concentrically arranged balloons. The balloons are inflated and evacuated to repeatedly collapse and expand an innermost balloon which is actually pumping the blood. US 2008/0103591 A1 proposes a foldable intravascularly insertable blood pump in which the impeller is a radially delivering impeller rather than an axially delivering impeller. Not only does the radially delivering impeller require a relatively low speed of approximately 5,000 to 15,000 rpm for delivering a typical amount of blood of approximately 2 to 5 l/min but, in addition, such a centrifugal pump does not require close radial tolerances between the impeller and the housing. This is due to the fact that the blood is radially expelled from the impeller blades against the circumferential wall of the housing and the wall redirects the blood flow from radial to axial. Consequently, there may be a large radial gap between the impeller blades and the circumferential housing wall. However, it is described that a gap between the front wall of the housing and the impeller blades and, if a back wall of the housing is present, between the back wall of the housing and the impeller blades is to be kept small at approximately 0.1 mm in order to prevent an undesired return flow of blood. This is described in relation to various embodiments, including one embodiment where the blades are held between two plates, the plates being attached to and radially extending from the drive shaft in spaced-apart relationship, and another embodiment where the blades are held between spokes rather than plates, the spokes being attached to and radially extending from the drive shaft.

Thus, while close tolerances between the impeller and the housing are not required in a radial direction, they are still required in the axial direction, thereby causing a risk of failure if the housing deforms towards the impeller under external loads or internal stresses.

It is therefore an object of the present invention to further reduce the risk of failure of radially delivering intravascular blood pumps, in particular foldable blood pumps as known from US 2008/0103591 A1.

According to the invention, the clearance between the front wall of the housing and the impeller is made sufficiently large to account for possible deflections of the housing wall, the minimum distance being at least 0.2 mm, preferably at least 0.3 mm, more preferably at least 0.4 mm, even more preferably at least 0.5 mm, yet more preferably at least 0.6 mm and most preferably 1 mm or more. It has been found that the throughput through the radially delivering impeller is sufficient to compensate any radial back flow axially before and/or behind the impeller blades by accordingly increasing the rotational speed of the drive shaft. This is no problem particularly where the axial length of the impeller blades is substantially greater than the clearance, e.g. 4 mm or more, preferably at least 5 mm, more preferably at least 6 mm and most preferably 7 mm or more. Power for driving the drive shaft is sufficiently available because the drive shaft is driven from outside the patient.

The aspect ratio ($L_{rotor}/D_{rotor}$) of the axial length ($L_{rotor}$) and average rotational diameter ($D_{rotor}$) of the impeller blades is preferably equal to or larger than 0.3 and, thus, substantially differs from typical centrifugal pumps whose aspect ratio would range below 0.2.

Along the length of the blades, the housing preferably tapers from a larger diameter at the back of the housing to a smaller diameter at the front of the housing. This taper plays a significant role in separating the inflow pressure from the outflow pressure and, therefore, reduces blood recirculation from the outflow towards the inflow. Considering the large clearance between the rotor and the housing walls, the taper is preferably larger than smaller, e.g. 5 degrees or more, preferably at least 7.5 degrees, more preferably at least 10 degrees and most preferably 12 degrees or more.

The invention is particularly useful with radially delivering impellers where the space between adjacent blades is open towards the front wall of the housing. This results in the pressure created between adjacent blades by the rotation of the impeller also being present next to the front wall, the front wall of the housing separating the impeller from the pump's low pressure side. Since the pressure in the blood flow between adjacent blades increases in a radially outward direction when the impeller rotates, the same pressure increase from radially inward to radially outward is present next to the front wall. Thus, when the space between adjacent blades is open towards the front wall, there is no negative radial pressure difference causing any significant radial back flow, contrary to what is suggested in US 2008/0103591 A1.

Therefore, a structure in which the blades are held between spokes (rather than plates) axially extending from the drive shaft is a particularly preferred embodiment according to the present invention. Alternatively, the blades can be arranged between a front plate and, possibly, a back plate radially extending from the drive shaft, provided that at least the front plate has through openings or perforations for pressure equalization towards the front wall of the housing. If the housing further has a back wall, such through openings or perforations are also provided in the back plate to provide for pressure equalization between the back plate of the impeller and the back wall of the housing.

The embodiment with the blades arranged between radially extending spokes is preferred over the embodiment with the blades held between perforated front and back plates, because a spoke-configuration can be folded about and/or along the drive shaft more easily. For similar reasons, the blades are preferably of planar configuration and may extend in a plane substantially parallel to the axis of rotation.

In essence, the impeller blades in the blood pump of the present invention swirls the blood around the drive shaft inside the housing. Due to the blood flow inlet being arranged radially inwardly (in the following also referred to as the "inlet diameter" of the impeller) relative to the radially outermost ends of the impeller blades (in the following also referred to as the "outlet diameter" of the impeller), i.e. preferably next to the drive shaft, the centrifugal forces acting on the swirling blood force the blood to flow radially outwards, thereby drawing in further blood through the inlet. The through flow is independent of the size of the gap between the impeller blades and the front wall and back wall of the housing. The structure of the blades is not critical either, provided that the swirling motion of the blood is sufficiently high to create the necessary centrifugal forces. The centrifugal forces generating the forward flow are directly related to the inlet versus outlet diameters. The larger the difference between the inlet diameter of the inlet orifices and the outlet diameter of the impeller blades is, the higher is the pressure gradient driving the forward flow.

While the invention is particularly useful with foldable intravascular blood pumps, it can likewise be realized in non-foldable blood pump types and would provide the same advantage that tolerances between the impeller housing and the impeller blades are not critical.

Where the housing has a back wall, the distance between the blades and the back wall of the housing is preferably in the same range as the distance between the blades and the front wall of the housing. However, where the blades are attached to the drive shaft via a back plate rather than spokes, the back plate of the impeller may replace the back wall of the housing and the outlet for the blood to exit the housing may be defined by a gap between the back plate of the impeller and the circumferential wall of the housing.

The redirection of flow of blood through the housing can be facilitated if the outer diameter of both the housing and the blades increases in an axial direction from the inlet side to the outlet side, which implies that the blood flow inlet and outlet are axially and radially spaced apart.

The housing itself is preferably made from a non-compliant polymer, preferably polyurethane, which is sufficiently flexible to be foldable about the drive shaft but retains a predetermined shape in its unfolded condition even at high internal pressures. It is particularly preferred to do without any frame structure, i.e. the housing is preferably formed substantially only by the non-compliant polymer film.

BRIEF DESCRIPTION OF THE DRAWINGS

Embodiments of the invention will now be described in greater detail with reference to the drawings, in which.

DETAILED DESCRIPTION OF THE PREFERRED EMBODIMENTS

Figure 1:
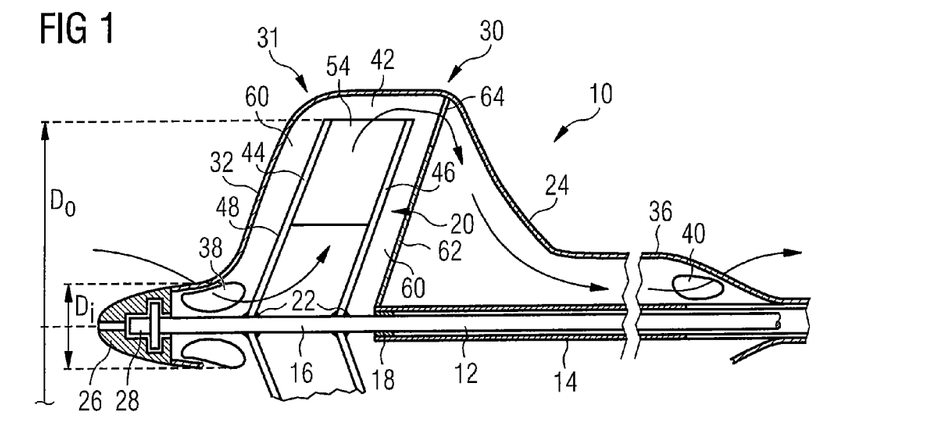
FIG. 1 shows a lateral sectional view of a first embodiment of a foldable intravascularly insertable blood pump.

FIG. 1 shows a blood pump according to a first embodiment comprising an elongate flexible bendable shaft 12 included in a catheter 14. The catheter 14 is defined by a flexible tube with a diameter of approximately 2.5 mm. The catheter 14 is preferably made of an abrasion-resistant polymer, such as polyamide or polyurethane, with an abrasion resistant inner lining of e.g. polyamide or polyimide. The flexible shaft 12 extends through the catheter 14. The shaft is conventionally defined by a multi-file wire bundle and can be made hollow for accepting a central guide wire 56, if desired (see the second embodiment shown in FIG. 3). The shaft 12 is driven at its proximal end by a motor (not shown), e.g. at 5,000 to 30.000 rpm, while the catheter 14 is retained in place. A speed of 30,000 rpm is permissible for a rotor with a small diameter not exceeding e.g. 7 mm. At the distal end, i.e. the left end in FIG. 1, the shaft 12 comprises a rigid portion 16. The distal end of the catheter 14 is connected with the shaft 12 via a sliding bearing 18. An impeller 20 is fastened to the rigid portion 16 of the shaft 12 via hinges 22 such that the impeller is foldable against the shaft 12. The impeller 20 and a distal portion of the shaft 12 and the catheter 14 are enclosed by a housing 24 made of a sack-like polyurethane skin and, thus, forming an envelope 24 around the impeller 20. Polyurethane is a non-compliant material and further allows a good connection between the envelope 24 and the catheter 14. The distal end of the envelope 24 comprises a hub 26 in which the distal end 28 of the shaft 12 is supported. The shaft cannot be axially displaced but is adapted to rotate in the hub 26 such that the envelope 24 is secured against rotation with the rotating shaft 12.

The envelope 24 comprises an annular bulge 30 in the region of the impeller 20, the impeller rotating in said bulge. The distal portion of the envelope 24 comprising the bulge 30 and the impeller 20 defines a pump head 31. In the distal region of the bulge 30 the envelope 24 comprises a concentric front wall 32 which is arranged at a large distance of between 0.5 and 1 mm from the distal side of the impeller 20. The bulge 30 may be reinforced and stretched by concentrically arranged elastic polymer or metal bars (not shown in FIG. 1) that are shaped to a desired geometry when deployed. For example, there can be used for such an application a shape-memory metal such as Nitinol which is pre-shaped to a desired geometry to match the rotor shape and the desired clearance between the impeller 20 and the envelope 24. It is preferable to use a minimal frame structure that occupies the least space when folded and to partially rely on the pressure built up in the envelope 24 by the centrifugal forces acting on the blood and building up pressure in the envelope 24 when the impeller 20 rotates. At the proximal side of the bulge 30 the envelope 24 comprises an elongate cylindrical extension 36. In this embodiment the outer diameter of the cylindrical extension 36 is smaller than that of the bulge 30. In the distal and the proximal regions of the envelope 24 rear and front flow openings 38 and 40 are provided, the front flow opening 38 being an inlet opening and the rear flow opening 40 being an outlet opening. Between the radially outer end of the impeller 20 and the envelope 24 an annular deflection channel 42 is defined during operation of the blood pump, through which deflection channel the radially delivered blood flows and is deflected in an axial direction.

The impeller 20 comprises two substantially parallel supporting structures 44 and 46 which are permanently connected, at a distance of >2 mm for example, with the rigid portion 16 of the shaft 12 via hinges 22. Each supporting structure 44, 46 is defined by six spokes 48, shown in FIG. 2. Thus, the angle between mutually adjacent spokes 48 is approximately 60°. The spokes 48 define a spoke wheel in each case. The spokes 48 of the spoke wheels are congruent. Between the congruent spokes 48 of the two supporting structures 44, 46 blades 54 of sail-like polymer skins are arranged.

Figure 2:
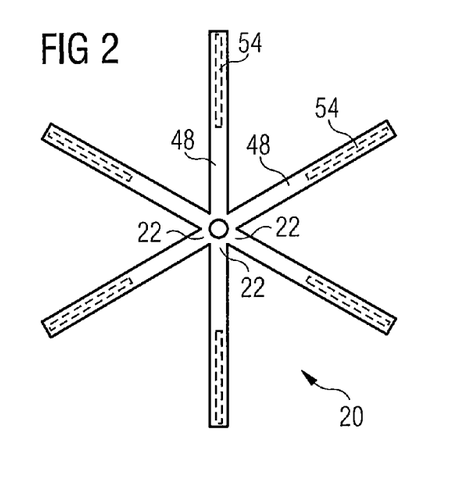
FIG. 2 shows a front view of the impeller of the embodiment shown in FIG. 1.

In a similar embodiment, fewer spokes, such as only two spokes, can be arranged, thereby providing a minimum amount of material needing to be compressed when folded, while accepting a slightly less efficient rotor design. Thus, a slightly higher rotational speed (above 4,000 rpm) may be required to generate the same amount of swirl.

The impeller 20 rotates within a chamber formed partly by the envelope 24 and partly by a partition wall or rear wall 62. Blood flow inlet openings 38 are formed in the envelope 24 at the distal end of the chamber in which the impeller 20 rotates and blood flow outlet openings 64 are formed in the rear wall 62. While the blood flow inlet openings 38 are arranged in radial proximity to the shaft 12, the outlet openings 64 in the rear wall 62 are arranged at a maximum radial distance from the shaft 12. Due to the centrifugal forces acting on the blood when the impeller 20 rotates, blood is drawn in through the radial inner inlet openings 38 and expelled through the radially outer outlet openings 64 into the cylindrical extension 36 of the envelope 24 from which the blood exits through the rear flow opening 40.

The size of the envelope 24 relative to the size of the impeller 20 is chosen such that there are two large gaps 60 between the front supporting structure 44 and the distal front wall 32 of the envelope 24, on the one hand, and between the rear supporting structure 46 and the partition or rear wall 62, on the other hand. Furthermore, the deflection channel 42 also provides a wide clearance between the radially outer border of the impeller 20 and the circumferential wall or bulge 30 of the envelope 24. Deflections of the envelope 24 towards the impeller 20 under external loads or internal stresses will not cause any contact with the impeller 20.

The gaps 60 before and behind the supporting structure 44, 46 of the impeller 20 are maintained by the pressure built up when the impeller 20 rotates within the chamber or by a combination of the pressure built up and elastic polymer or metal frame structures in the front wall 32 and/or rear wall 62. Due to the rotation of the impeller 20 and the centrifugal forces acting on the blood and forcing the blood to flow from radially inward towards radially outward, the pressure inside the chamber also increases from radially inward towards radially outward. Since the space between adjacent blades 54 is open to the gaps 60, this pressure acts against both the partition or rear wall 62 and the front wall 32 of the envelope 24, thereby keeping the rear wall 62 and the envelope 24 spaced from the impeller 20.

Figure 3:
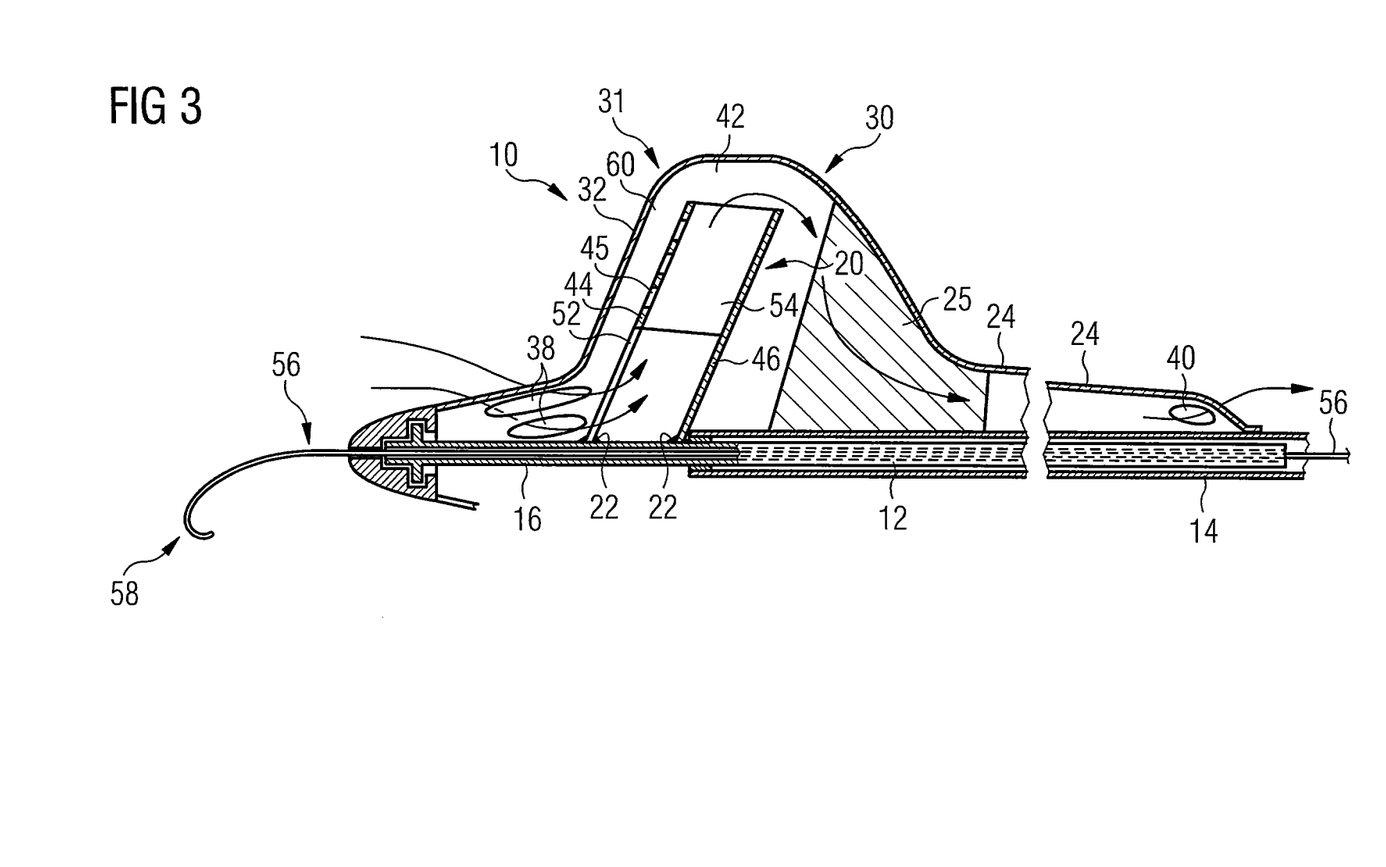
FIG. 3 shows a lateral sectional view of a second embodiment of the blood pump.

A second embodiment of the blood pump is shown in FIG. 3. A guide wire 56 extends through the shaft 12, the end 58 of said guide wire being "J-" shaped and possibly "pigtail"-shaped, wherein the blood pump 10 can be inserted into the heart via said guide wire 56. Before operation, the guide wire 56 is removed. Such guide wire 56 may likewise be used in the other embodiments described herein.

The second embodiment shown in FIG. 3 further differs from the first embodiment shown in FIG. 1 by the structure of the impeller 20, more particularly by its front and rear supporting structures 44, 46. Firstly, the rear supporting structure 46 is formed as a plate which may be formed by the six spokes 48 interconnected by a polymer skin to define a back plate which replaces the partition or rear wall 62 of the first embodiment shown in FIG. 1.

Secondly, the front supporting structure 44 is also formed as a plate, e.g. with a polymer skin mounted between the spokes 48. However, the front supporting structure 44 includes openings 45 to ensure pressure equalization from the space between adjacent blades 54 towards the gap 60 between the front supporting structure 44 and the front wall 32 of the envelope 24. As explained, this pressure equalization helps to maintain the width of the gap 60 by pressing the walls of the envelope 24 outwardly and thereby expanding the envelope 24 to its maximum size.

Thirdly, a plurality of stationary vanes 25 are arranged in the envelope 24 about the catheter 14 proximally from the rear supporting structure 46 in order to withdraw swirl from the blood flow and thereby increase the blood pressure even further. The stationary vanes 25 extend along the length of the catheter 14, their inlet ends being inclined towards the blood flow swirl to improve laminar flow without eddying. Such stationary vanes 25 can also be advantageous in respect of the other embodiments described hereinbefore and hereinafter.

Figure 4:
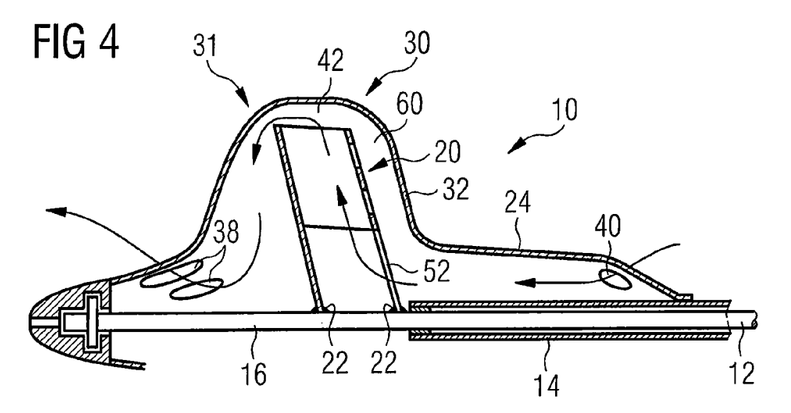
FIG. 4 shows a lateral sectional view of a third embodiment of the blood pump with the impeller raised in a direction opposite to that shown in FIG. 3 and with an opposite delivering direction.

FIG. 4 shows a third embodiment of the blood pump 10, which differs from the second embodiment in FIG. 3 in that the impeller 20 extends from the shaft at a negative rather than a positive angle, here approximately −70°. Thus, the blood flows within the blood pump 10 in the reverse direction as compared with FIG. 3. The pumping action is effective from the proximal end to the distal end. The blood flows through the rear flow opening 40 into the blood pump 10 and leaves the blood pump 10 through the front flow openings 38. In this embodiment the narrow proximal part of the envelope 24 may have to be radially supported with a stent-like structure to prevent collapse should the swirl in front of the impeller not be sufficient to keep it radially stable.

The blood pumps 10 described so far are substantially identical to the blood pump described in US 2008/0103591 A1, except for the sizes of the impeller 20 and envelope 24 and, in particular, the gaps 60 formed distally and proximally between the impeller 20 and the envelope 24. Further details of how the pumps 10 are driven, folded and unfolded are described in US 2008/0103591 A1.

Figure 5:
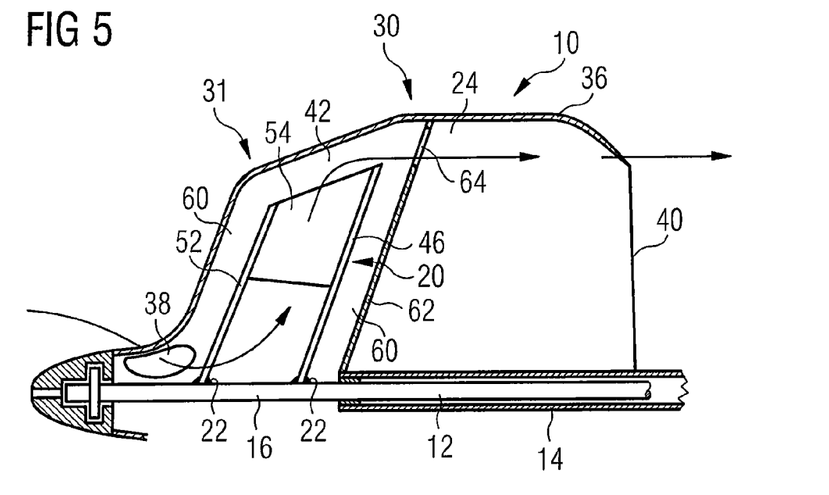
FIG. 5 shows a fourth embodiment of the blood pump similar to the embodiment shown in FIG. 1 with a different shape of the impeller housing.

A fourth embodiment will now be described in relation to FIG. 5. This embodiment is similar to the first embodiment shown in FIG. 1, except that the envelope 24 has a skirt-like extension 36. Here the outer diameter of the bulge 30 does not decrease proximally from the impeller 20 but remains substantially constant to form a large rear flow opening 40. A blood pump with a skirt-like envelope 24 as shown in FIG. 5 consumes less energy because the blood flow does not have to be redirected radially inward towards the shaft 12. However, a short neck portion with a slightly reduced diameter at the proximal end or outflow opening 40 of the skirt-like extension 36 is advantageous so as to maintain the pressure inside the skirt-like envelope 24 above the outside pressure and, thus, avoid fluttering or even collapse of the skirt-like extension 36. Again, the partition or rear wall 62 can be dispensed with if the rear supporting structure 46 is formed as a plate, as described above in relation to the second embodiment shown in FIG. 3. This can even be advantageous because an impeller with a rotating rear plate would be in contact with and cause movement of the blood right behind, i.e. proximal from, the impeller 20, thereby decreasing the risk of thrombosis.

A second difference in the fourth embodiment shown in FIG. 5 as compared to the previously described embodiments is that the impeller 20 has an outer diameter increasing from the inflow end towards the outflow end. This structure supports blood flow in the desired direction, here from distal to proximal, and offers a maximized discharge diameter, thereby increasing the delivery rate.

Figure 6:
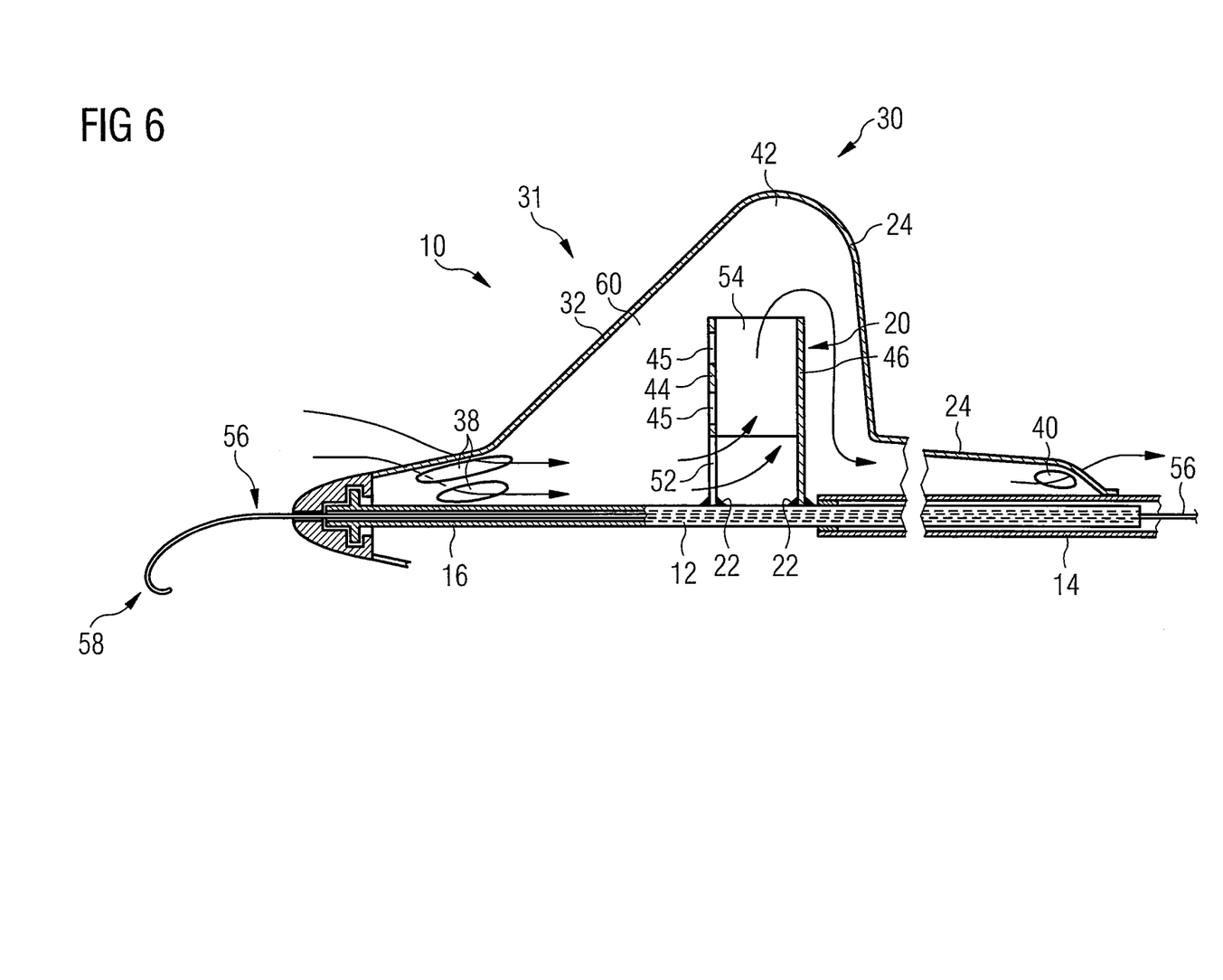
FIG. 6 shows a fifth embodiment of the blood pump similar to the embodiment shown in FIG. 5 with a different location of the impeller.

A fifth embodiment is shown in FIG. 6. It differs from the previous embodiments mainly by the impeller 20 being positioned further away from the blood flow inlet openings 38. This arrangement provides the advantage that blood flowing through the inlet openings 38 will have no swirl when entering axially, the swirl of the blood being created inside the housing 24. When the impeller 20 is arranged closer to the blood flow inlet openings 38, as in the previous embodiments, the swirl imposed on the blood by the impeller 20 will be partly imparted through the inlet openings 38 onto the blood outside the housing 24, due to the high viscosity of the blood. This causes energy losses. The arrangement further away from the inlet openings 38, as shown in FIG. 6, avoids such energy losses.

Figure 7:
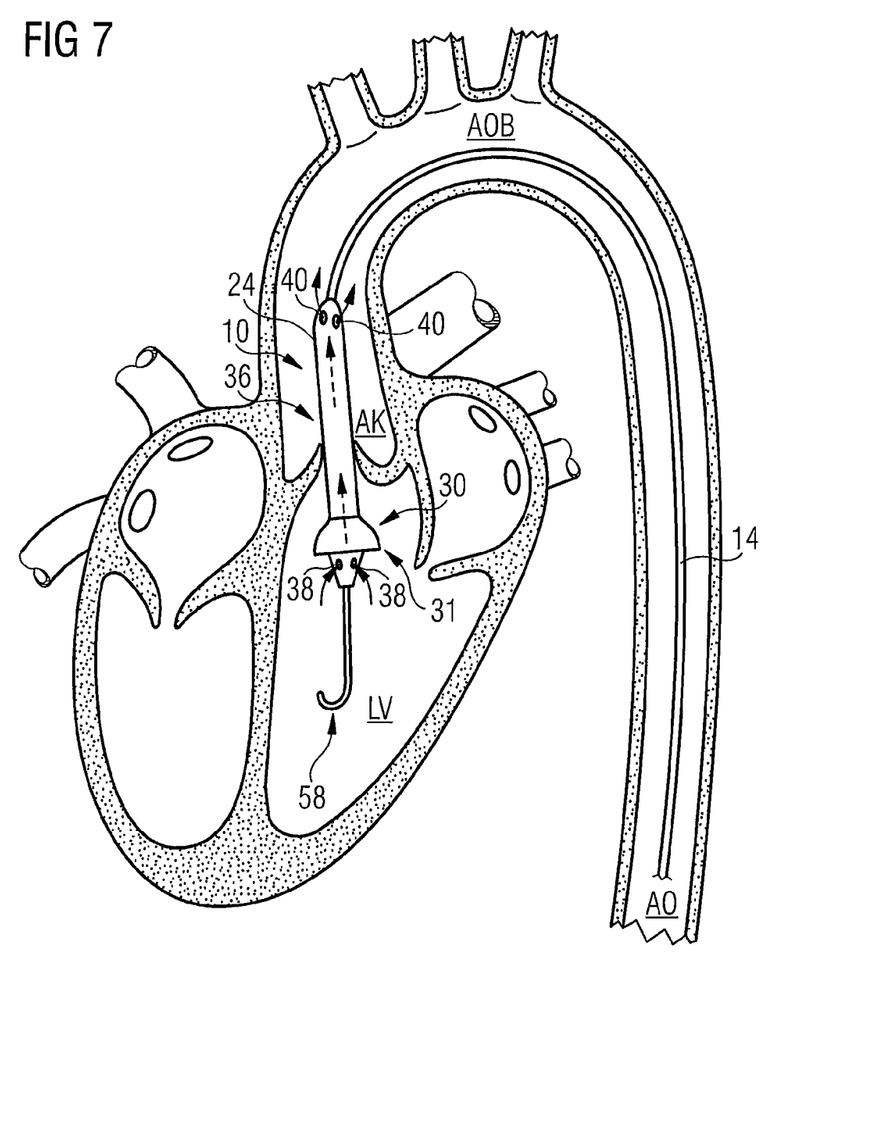
FIG. 7 shows a first embodiment of inserting the blood pump (of FIG. 3) into the human heart.
Figure 8:
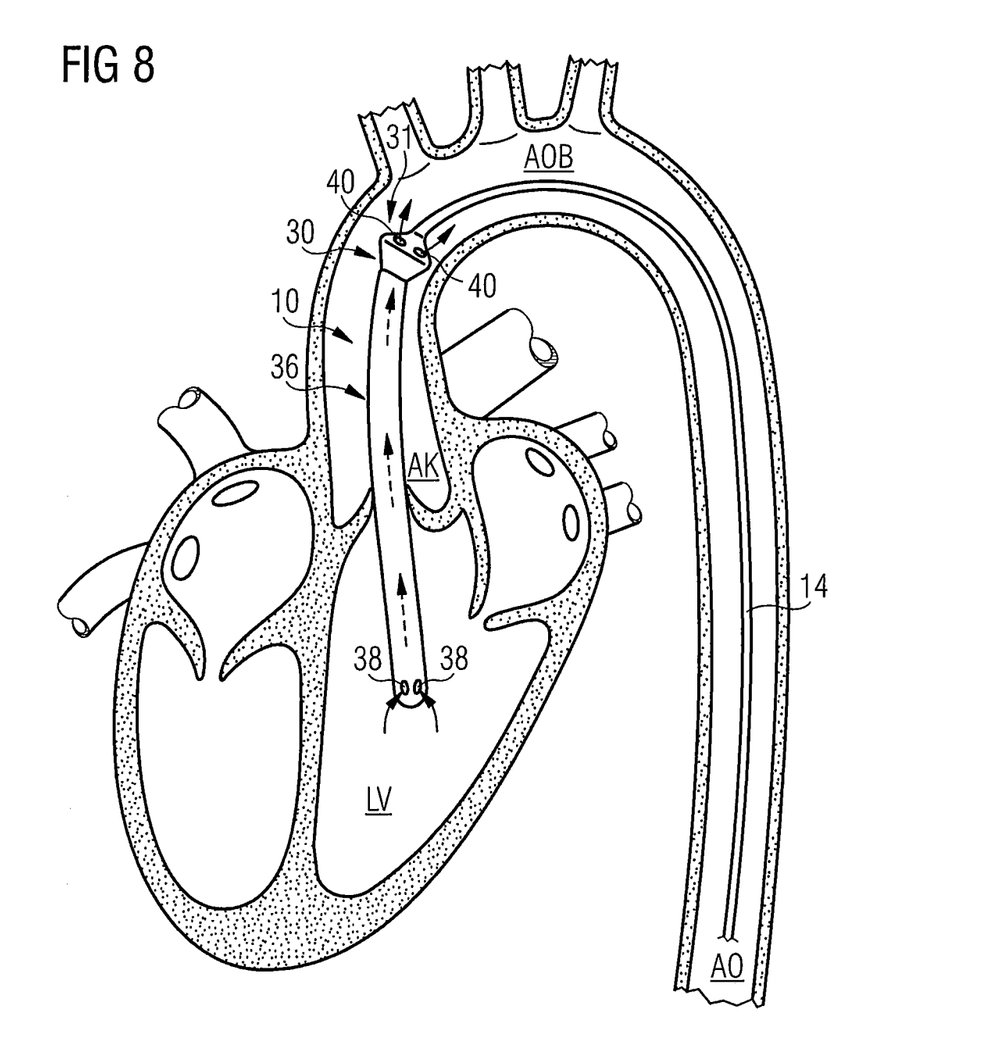
FIG. 8 shows a second embodiment of the blood pump within the human heart.
Figure 9:
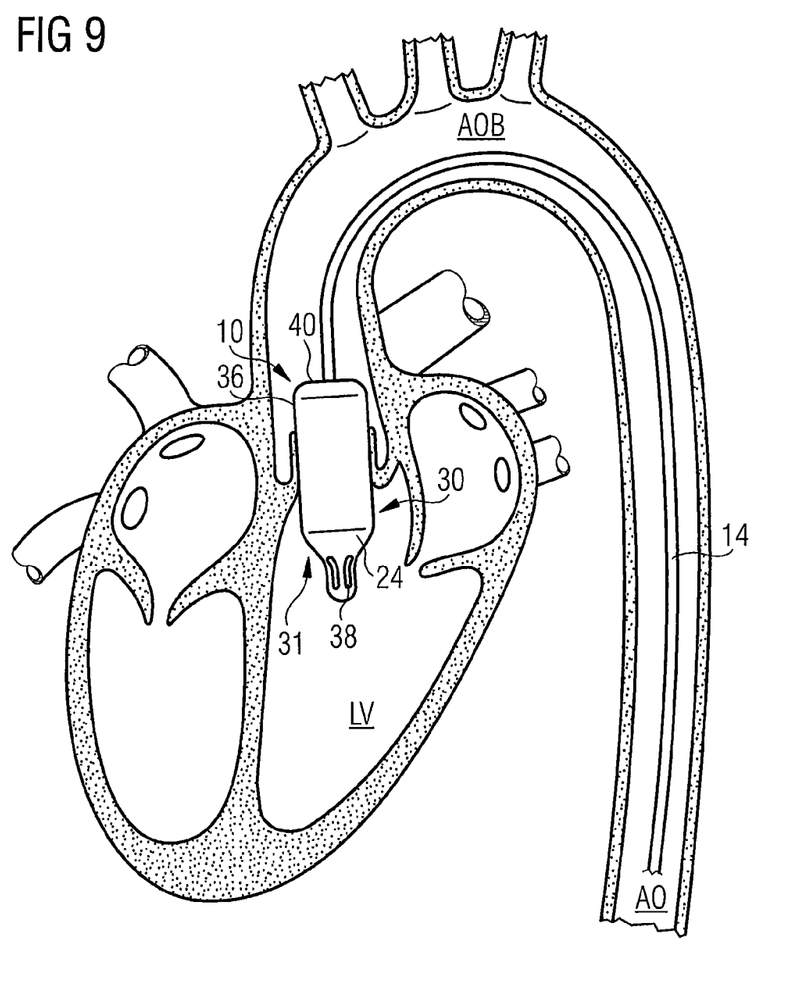
FIG. 9 shows a third embodiment of inserting the blood pump (of FIG. 5) into the patient heart.

FIGS. 7 to 9 show different methods of placing the blood pump in the heart. FIG. 7 shows the blood pump 10 according to the first and second embodiments of FIGS. 1 to 3. The blood pump 10 is arranged such that the pump head 31 comprising the distally arranged inflow openings 38 is located in the left ventricle LV, and the rear pump region comprising the proximally arranged outflow openings 40 is located inside the aorta AO in front of the aortic arch AOB. The cylindrical extension 36 of the envelope 24 has a length of approximately 60 to 80 mm. The aortic valve AK surrounds the cylindrical extension 36. The blood pump 10 delivers the blood in the forward direction from the distal end to the proximal end from the left ventricle LV into the aorta AO. The blood flows through the distal flow openings 38 into the envelope 24 of the blood pump 10. The rotating impeller accelerates the blood inside the bulge 30 of the envelope 24 and pumps the blood into the cylindrical extension 36 of the envelope 24. The blood leaves the blood pump 10 through the proximal flow openings 40.

FIG. 7 shows an extension of the hard tip 26 in the form of a "pigtail" with the aid of which the blood pump 10 is supported on the myocardium for keeping a minimum distance between the suction region of the blood pump 10 and the inner wall of the myocardium.

FIG. 8 shows a method of placing a proximally arranged blood pump 10. The distal end of the blood pump comprising the flow openings 38 is located in the left ventricle LV inside the heart. The pump head 31 comprising the proximal flow openings 40 and the bulge 30 including the impeller 20 is located inside the aorta AO distally of the aortic arch AOB. The catheter 14 including the drive shaft 12 extends through the aortic arch AOB. In the region of the aortic arch AOB the flexible shaft 12 is bent. The aortic valve AK surrounds the cylindrical extension 36 of the blood pump envelope 24 arranged upstream as seen in the direction of delivery. The length of the cylindrical extension 36 is approximately 60 to 80 mm. The blood pump 10 delivers the blood in the same manner as the pump shown in FIG. 6, i.e. from the distal end to the proximal end from the left ventricle LV into the aorta AO. The blood enters the cylindrical extension 36 of the blood pump envelope 24 through the distal flow openings 38, the extension 36 being located upstream and being radially reinforced as compared with the pump 10 shown in FIG. 7, and is taken in and accelerated by the impeller 20 (not shown) in the bulge 30 of the envelope 24. Inside the aorta AO and in front of the aortic arch AOB the accelerated blood flows out through the front flow opening 40. Here, again, an extension distal of the inlet openings 38 in the form of a pigtail 58 can be added.

FIG. 9 shows the method of placing the blood pump 10 according to the fourth embodiment of FIG. 5. The blood pump 10 is arranged such that the pump head 31 comprising the distally arranged flow openings 38 is located in the left ventricle LV, and the rear pump region comprising the skirt-like cylindrical extension 36 with the large proximally arranged outflow opening 40 is located inside the aorta AO in front of the aortic arch AOB. The cylindrical extension of the envelope 24 has a length of approximately 40 mm to 60 mm. The aortic valve AK surrounds the cylindrical extension 36. The blood pump 10 delivers the blood in the forward direction from the distal end to the proximal end from the left ventricle LV into the aorta AO. The blood flows through the distal flow openings 38 into the envelope 24 of the blood pump 10. The rotating impeller accelerates the blood inside the bulge 30 of the envelope 24 and pumps the blood into the cylindrical extension 36 of the envelope 24. The blood leaves the blood pump 10 through the proximal outflow opening 40.

Figure 10:
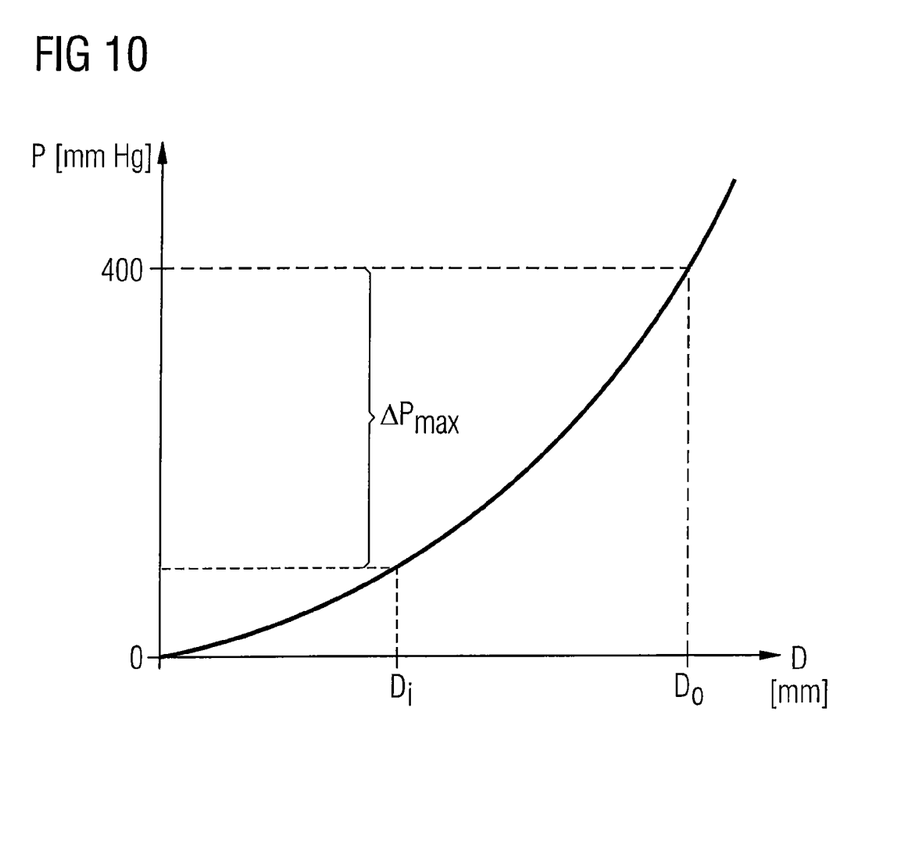
FIG. 10 is a schematic diagram illustrating the centrifugal principle.

FIG. 10 illustrates the principle of how the driving pressure is generated in the centrifugal pumps described hereinbefore. As can be seen in FIG. 1, the radially outermost part of the inlet openings 38 defines a maximum inner diameter $D_i$ and the radially outermost end of the blade 54 defines an outer diameter $D_o$. Due to the rotational speed the blade 54 and, thus, the speed imposed on the blood creates a pressure difference $\Delta p_{max}$ which may be calculated as follows:

$$\Delta p_{max} \approx \rho/2[V^2_{rotor-outlet} - V^2_{rotor-inlet}] \approx \rho/2(\omega^2[D_o/2]^2 - [D_i/2]^2)$$

where $\omega$ is the angular velocity of the shaft 12. The curve shown in FIG. 10 illustrates this principle with $\omega$ constant. The pressure difference $\Delta p_{max}$ therefore approximately corresponds to the blood pressure differential between the inlet openings 38 and the radially outer ends of the blades 54 (FIG. 1).

The invention claimed is:

1. An intravascularly insertable blood pump, comprising:
   a rotor having an axis of rotation and at least one blade arranged about the axis of rotation so as to form a radially delivering impeller,
   a flexible shaft extending through a catheter and adapted to drive the rotor, and
   a housing in which the impeller is arranged for rotation, the housing having a blood flow inlet arranged radially inwardly relative to a radially outer end of the at least one blade with respect to the axis of rotation,
characterized in that a first axial distance between a front wall of the housing and the impeller is 0.3 mm or more.

2. The blood pump according to claim 1, wherein the first axial distance is at least one of 0.4 mm, 0.5 mm, 0.6 mm, and 1 mm or more.

3. The blood pump according to claim 1, wherein the housing further has a back wall and wherein a second axial distance between the back wall and the impeller is 0.3 mm or more.

4. The blood pump according to claim 3, wherein the second axial distance is at least one of 0.4 mm, 0.5 mm, 0.6 mm, and 1 mm or more.

5. The blood pump according to claim 1, wherein the at least one blade and the housing are foldable and unfoldable between a first configuration of reduced diameter and a second, operational configuration of increased diameter.

6. The blood pump according to claim 1, wherein the blood flow inlet and a blood flow outlet of the housing are axially spaced apart.

7. The blood pump according to claim 6, wherein an outer diameter of both the housing and the at least one blade increases in an axial direction from the blood flow inlet to the blood flow outlet.

8. The blood pump according to claim 1, wherein the at least one blade has an axial length of at least one of 2 mm, 4 mm, 5 mm, 6 mm and 7 mm or more.

9. The blood pump according to claim 1, wherein the at least one blade has a planar configuration.

10. The blood pump according to claim 1, wherein the housing is made from at least one of a non-compliant polymer and polyurethane.

11. The blood pump according to claim 10, wherein the housing lacks a frame structure.

12. The blood pump according to claim 1, wherein a space defined between adjacent blades is open towards the front wall of the housing.

13. The blood pump according to claim 1, comprising one or more stationary vanes within the housing, the vanes being arranged behind the impeller in the direction of blood flow and extending along the catheter.

14. The blood pump according to claim 1, wherein the housing has a skirt-like extension with a neck-like portion of reduced diameter at an outflow end thereof.

15. The blood pump according to claim 1, wherein the at least one blade has an aspect ratio of 0.3 or more, the aspect ratio being defined as $$L_{rotor}/D_{rotor},$$

where $L_{rotor}$ is the axial of the blade and $D_{rotor}$ is the average rotational diameter of the blade.

* * * * *

UNITED STATES PATENT AND TRADEMARK OFFICE
CERTIFICATE OF CORRECTION

| | | |
|---|---|---|
| PATENT NO. | : 9,533,084 B2 | Page 1 of 1 |
| APPLICATION NO. | : 14/371154 | |
| DATED | : January 3, 2017 | |
| INVENTOR(S) | : Siess et al. | |

It is certified that error appears in the above-identified patent and that said Letters Patent is hereby corrected as shown below:

In the Claims

At Column 10, Claim number 15, Line number 41, "axial of" should be --axial length of--.

Signed and Sealed this
Seventh Day of March, 2017

Michelle K. Lee
*Director of the United States Patent and Trademark Office*